(12) United States Patent
Ueyama et al.

(10) Patent No.: US 7,541,484 B2
(45) Date of Patent: Jun. 2, 2009

(54) PROCESS FOR PRODUCING PHOSPHATE

(75) Inventors: Norio Ueyama, Wakayam (JP); Yoshifumi Nishimoto, Wakayam (JP)

(73) Assignee: Kao Corporation, Tokyo (JP)

( * ) Notice: Subject to any disclaimer, the term of this patent is extended or adjusted under 35 U.S.C. 154(b) by 245 days.

(21) Appl. No.: 11/302,111

(22) Filed: Dec. 14, 2005

(65) Prior Publication Data

US 2006/0142605 A1 Jun. 29, 2006

(30) Foreign Application Priority Data

Dec. 22, 2004 (JP) .............................. 2004-371311

(51) Int. Cl.
*C07F 9/02* (2006.01)

(52) U.S. Cl. ...................... 558/110; 558/104

(58) Field of Classification Search ................ 558/104, 558/110
See application file for complete search history.

(56) References Cited

U.S. PATENT DOCUMENTS

2003/0065205 A1* 4/2003 Tsuyutani et al. ............. 558/71

FOREIGN PATENT DOCUMENTS

| EP | 1 435 358 A2 | 7/2004 |
| JP | 38-12524 | 7/1963 |
| JP | 60-43076 | 9/1985 |
| JP | 62-25155 | 6/1987 |
| JP | 3-27558 | 4/1991 |
| JP | 5-66958 | 9/1993 |
| JP | 11-158193 | 6/1999 |

* cited by examiner

*Primary Examiner*—Jafar Parsa
(74) *Attorney, Agent, or Firm*—Oblon, Spivak, McClelland, Maier & Neustadt, P.C.

(57) ABSTRACT

The invention relates to a process for producing a phosphate, which includes reacting a phosphorus pentaoxide-containing phosphorylating agent with an organic hydroxy compound, the reaction being carried out at a reaction temperature of 50 to 70° C. until the degree (w) of remaining phosphorus pentaoxide undissolved in a reaction solution, defined by the following equation (1), is reduced to 15 wt % or less:

$$W=[1-(AV_t-AV_p)/AV_0]\times 100 \tag{1}$$

wherein W is the degree [wt %] of remaining phosphorus pentaoxide undissolved in a reaction solution; $AV_t$ is the acid value [mg KOH/g] of the reaction solution excluding undissolved phosphorus pentaoxide in an arbitrary time; $AV_p$ is the theoretical acid value [mg KOH/g] of the phosphorylating agent excluding undissolved phosphorus pentaoxide; and $AV_0$ is the theoretical acid value [mg KOH/g] of phosphorus pentaoxide.

9 Claims, No Drawings

PROCESS FOR PRODUCING PHOSPHATE

FIELD OF THE INVENTION

The present invention relates to a process for producing a phosphate useful in a shampoo, a detergent, a facial wash etc.

BACKGROUND OF THE INVENTION

A phosphate of an organic hydroxy compound (hereinafter referred to simply as "phosphate") is used in fields such as detergents, emulsions, fiber-treating agents, rust preventives and medical supplies. Particularly, an alkali salt metal such as a sodium or potassium monoalkyl phosphate having a long-chain alkyl group, and an alkanol amine salt such as triethanol amine, are water-soluble and excellent in foaming power and detergency with less toxicity and less skin simulation, and are thus useful in commodities applied directly onto the human body, such as shampoos and facial washes. When such commodities applied directly to the human body are compounded with phosphates, it is important for qualities that the phosphates have less color and less smell.

The phosphates can be produced by reacting an organic hydroxy compound with a phosphorylating agent such as orthophosphoric acid, polyphosphoric acid and phosphorus pentaoxide. In the reaction of the phosphorylating agent with the organic hydroxy compound, however, significant coloration occurs and a smell different from that of the starting organic hydroxy compound is generated. Accordingly, troublesome steps for removing coloring components and smelling components are necessary after the phosphorylation reaction.

As a method of removing coloring components and smelling components, there is proposed a method of separating a phosphate by re-crystallization using a solvent (JP-A 11-158193) or a method which includes converting a phosphate with a basic compound into a phosphate salt and then using a solvent to extract smelling components into an organic layer and the phosphate salt into an aqueous layer (JP-B 3-27558).

As a method of preventing coloration in the phosphorylation reaction, there is proposed a method which includes adding a borohydride compound (JP-B 60-43076) or a method which includes adding phosphorous acid, hypophosphorous acid or the like (JP-B 38-12524).

As a method of deodorization without using a solvent, on the other hand, there is proposed a method which includes contacting with an inert gas such as water vapor in a thin-film deodorization column such as a rotary thin-film evaporator and a wetted-walled column (JP-B 62-25155) or a method wherein phosphorylation reaction is carried out while water vapor is blown in (JP-B 5-66958).

SUMMARY OF THE INVENTION

The present invention relates to a process for producing a phosphate, which includes reacting a phosphorus pentaoxide-containing phosphorylating agent with an organic hydroxy compound to produce a phosphate, the reaction being carried out at a reaction temperature of 50 to 70° C. until the degree (w) of remaining phosphorus pentaoxide undissolved in a reaction solution, defined by the following equation (1), is reduced to 15 wt % or less:

$$W=[1-(AV_t-AV_p)/AV_0] \times 100 \qquad (1)$$

wherein W is the degree [wt %] of remaining phosphorus pentaoxide undissolved in a reaction solution; $AV_t$ is the acid value [mg KOH/g] of the reaction solution excluding undissolved phosphorus pentaoxide in an arbitrary time; $AV_p$ is the theoretical acid value [mg KOH/g] of the phosphorylating agent excluding undissolved phosphorus pentaoxide; and $AV_0$ is the theoretical acid value [mg KOH/g] of phosphorus pentaoxide.

The present invention provides a phosphate with an antioxidant content of 20 ppm or less produced by the process described above.

DETAILED DESCRIPTION OF THE INVENTION

Because a solvent is used in a large amount in the methods in JP-A 11-158193 and JP-B 3-27558 supra, facilities etc. are necessary for recovering the solvent. In the method of separation by recrystallization, phosphates having alkyl distribution or phosphates having distribution in the number of moles of alkylene oxides added may change alkyl distribution and distribution of alkylene oxides added to the phosphates before and after the treatment, and may be problematic in compounding into products. Further, the loss of the phosphates into a solvent is inevitable. In the method of extraction with a solvent, a lower alcohol is necessary as a demulsifying agent in addition to the extraction solvent, and thus recovery of the solvent is troublesome, and costs for investment in facilities are increased. From the foregoing, the method of using these solvents has a disadvantage of higher costs because of lower productivity and higher costs for investment in facilities.

The methods in JP-B 60-43076 and JP-B 38-12524 supra have a disadvantage that the physical properties of the product phosphate are influenced by contamination of the phosphate with the additives.

When smelling components are removed by blowing an inert gas such as water vapor, the efficiency of contacting the phosphate with an inert gas such as water vapor is low and thus the effect of removal is low. For example, when deodorization is carried out with an apparatus in a batch system, the treatment time is prolonged, the productivity is lowered, and simultaneously the properties of the phosphate may be deteriorated due to decomposition. When the thin-film deodorization column is used in a continuous system, the efficiency of contacting is further lower than in the batch system, and the amount of an inert gas such as water vapor to be blown is increased, and the size of the apparatus is also increased, and thus the costs for investment in facilities are increased, thus resulting in higher costs. Waste water or exhaust gas is increased to increase treatment costs. There is no effect of improvement in hue, and coloration may be caused by heating.

Accordingly, there has been demand for development of an economically advantageous process for industrial production of a phosphate with less coloration and less nasty smell.

The present invention provides a process of easily and rapidly producing a phosphate with less coloration and less nasty smell.

A phosphate with less coloration and less nasty smell can be produced easily and rapidly according to the process of the present invention. In particular the invention provides a process for efficiently producing a phosphate excellent in hue and scent.

The phosphorylating agent used in the present invention contains phosphorus pentaoxide and may also contain orthophosphoric acid, polyphosphoric acid etc. in addition to phosphorus pentaoxide.

The organic hydroxy compound according to the present invention is an organic compound having a hydroxy group. The organic hydroxy compound includes, for example, linear or branched saturated or unsaturated alcohols, alkylene oxide adducts thereof (number of carbon atoms in the alkylene oxide: 2 to 4) etc., and these can be used alone or as a mixture of two or more thereof. Among these, a C6 to C30 alcohol and a polyoxyalkylene alkyl ether having 1 to 10 moles on the average of a C2 to C4 alkylene oxide added to the alcohol are preferable. Further, an alcohol/alkylene oxide adduct (number of carbon atoms in the alkylene oxide: 2 to 4) has a significant effect on suppression of coloration, and particularly a polyoxyalkylene alkyl ether having 1 to 5 moles on average of C2 to C4 alkylene oxide added to a C8 to C14 alcohol is particularly preferable.

The ratio of the phosphorylating agent to the organic hydroxy compound used in the present invention is not particularly limited, but from the viewpoint of reducing the amount of the unreacted remaining hydroxy compound and suppressing the decomposition of a phosphate formed during the reaction, the phosphorylation reaction is carried out preferably under the conditions wherein the value R represented by the following equation (2) is 2.8 to 3.2, more preferably under the conditions wherein R is 2.9 to 3.1.

$$R=(X+Z)/Y \qquad (2)$$

wherein X represents the number of moles of the organic hydroxy compound subjected to the reaction, and when the phosphorylating agent is expressed in the form of $P_2O_5 \cdot nH_2O$, Y represents the number of moles of $P_2O_5$ in the phosphorylating agent subjected to the reaction, and Z represents the number of moles of $H_2O$.

Suppression of coloration and smell of the phosphate in the phosphorylation reaction of the present invention is related considerably to the reaction temperature and the degree of remaining phosphorus pentaoxide undissolved in the reaction solution. That is, an increase in the reaction temperature at the stage where phosphorus pentaoxide is undissolved leads to an increase in topical reaction activity on the surface of undissolved phosphorus pentaoxide, to cause coloration and smell. Accordingly, the reaction is carried out at a reaction temperature of 50 to 70° C. in the present invention until the degree (w) of remaining phosphorus pentaoxide undissolved in the reaction solution, defined by the equation (1) above, is reduced to 15 wt % or less, preferably 10 wt % or less, more preferably 5 wt % or less. Side reaction can thereby be prevented, and a phosphate with less coloration and less nasty smell can be obtained in a usual agitating bath.

The degree (W) of remaining phosphorus pentaoxide undissolved in the reaction solution can be easily determined by measuring the acid value of the reaction solution in the following manner.

1) A reaction solution sample, which was mixed in an arbitrary time, is collected.
2) Phosphorus pentaoxide undissolved in the reaction solution sample is removed by a method such as filtration.
3) The acid value (first equivalence point) of this reaction solution is determined as $AV_t$ by potentiometric titration.
4) On the basis of the acid value $AV_t$, the degree (W) of remaining undissolved phosphorus pentaoxide is determined according to the equation (1) above.

In the present invention, the reaction between the phosphorylating agent and the organic hydroxy compound is carried out preferably in an atmosphere at a low partial pressure of oxygen. The atmosphere at a low partial pressure of oxygen is an atmosphere in which the amount of oxygen in the reactor is decreased by reducing the partial pressure of oxygen in a gaseous phase to a pressure being lower than that in air, and from the viewpoint of suppressing coloration and smell, the phosphorylation reaction is carried out preferably in an atmosphere where the partial pressure of oxygen in a gaseous phase is ¼ or less, particularly ¹⁄₁₀ or less, relative to that in air.

As the method of reducing the amount of oxygen in the reaction container, there is a method which involves replacing or reducing oxygen by an inert gas or a method which involves conducting the reaction under reduced pressure at 25 kPa or less. The method of using an inert gas is preferable because the procedure can be carried out at atmospheric pressure and from the viewpoint of charging phosphorus pentaoxide as powder. The inert gas includes argon, nitrogen etc. which do not react with the organic hydroxy compound and the phosphorylating agent, and nitrogen is preferable from an economical viewpoint. There is a method wherein prior to the reaction, oxygen-containing air is replaced by an inert gas to reduce the partial pressure of oxygen, or a method wherein an inert gas is blown in a gaseous or liquid phase of the reaction during the reaction at atmospheric pressure or under reduced pressure. When an inert gas is blown in a gaseous or liquid phase of the reaction during the reaction, the amount of the inert gas introduced is preferably 0.0001 to 0.5 m³/h·kg per kg of the total amount of the organic compound, the phosphorylating agent etc. charged. In the present invention, the amount of an inert gas (m³/h·kg)" is a flow rate under standard conditions (temperature 0° C., pressure 101.3 kPa).

In the phosphorylation reaction of the present invention, the order of addition of the starting materials is not particularly limited, but because the heat of reaction of phosphorus pentaoxide is high, a method of adding phosphorus pentaoxide to the organic hydroxy compound is preferable from the viewpoint of regulating the reaction temperature. After the reaction is carried out at a reaction temperature of 50 to 70° C. until the degree (W) of remaining undissolved phosphorus pentaoxide is reduced to 15 wt % or less as described above, an aging reaction is carried preferably at 75 to 120° C., more preferably at 80 to 95° C. The reaction time is determined depending on reaction temperature and can thus not be generalized, but from the viewpoint of reducing the amount of the remaining organic hydroxy compound, the reaction time is preferably 3 to 20 hours, more preferably 5 to 15 hours.

In the phosphate obtained by the phosphorylation reaction, there is a pyrophosphoric acid compound derived from the phosphorylating agent, and for decomposing this pyrophosphoric acid compound, hydrolysis with water or water vapor added is preferably carried out at 50 to 100° C. for 0.5 to 10 hours.

In the present invention, an antioxidant may not be added.

When an antioxidant is contained in the phosphate, there is a disadvantage that deterioration in smell of the phosphate is caused. Accordingly, the content of the antioxidant in the phosphate is preferably 20 ppm or less, more preferably 10 ppm or less.

The antioxidant may be BHT (butyl hydroxy toluene), phosphorous acid, hypophosphorous acid or the like.

The phosphate of an organic hydroxy compound, obtained in the process of the present invention, has less coloration and less smell, and can thus be used preferably in fields such as detergents, emulsions, fiber-treating agents, rust preventives and medical supplies, more specifically as shampoos, detergents, facial washes etc.

EXAMPLES

Hereinafter, the present invention is described by reference to the Examples. The Examples are provided for merely illustrating the present invention and not intended to limit the present invention.

In the following examples, measurement of hue and evaluation of smell were carried out by the following methods.

<Method of Measuring Hue>

An obtained phosphate was diluted 10-fold with ethanol and then measured for its absorbance at a wavelength of 420 nm with spectrophotometer U-3300 manufactured by Hitachi High Technologies, and a value obtained by multiplying the determined absorbance by 1000 was expressed as "KLETT NO". A lower value is judged to be excellent with less coloration.

<Method of Evaluating Smell>

50 mL of an obtained phosphate was introduced into a 110-mL wide-mouthed glass bottle, and skilled examiners directly smelled the opening of the bottle to evaluate smell under the following criteria:

○: There is no nasty smell.
Δ: A nasty smell is slightly felt.
x: There is an evident nasty smell.

Example 1

609.9 g alcohol (2.56 moles; the hydroxyl value (OHV) of this alcohol was 235.1; the molecular weight, 238.66) having 1 mole on average of ethylene oxide added thereto (KALCOL 2470 manufactured by Kao Corporation) was introduced into a 2-L separable glass container previously purged sufficiently with nitrogen, and then nitrogen was introduced at a rate of 9 mL/min. through a dip tube. Thereafter, 81.5 g of 85% aqueous phosphoric acid solution (orthophosphoric acid) ($P_2O_5$, 0.35 mol; $H_2O$, 1.74 moles) was added thereto, and the mixture was heated to 40° C. and stirred for 30 minutes. Then, 158.7 g phosphorus pentaoxide (99% purity) ($P_2O_5$, 1.11 moles; $H_2O$, 0.09 mole) was added in suitably divided portions, paying attention to the heat of reaction such that the temperature in the bath did not exceed 65° C. R in this case was 3.00 (wherein X=2.56, Y=1.46, Z=1.83).

After addition of phosphorus pentaoxide was finished, the temperature was regulated so as to maintain 65° C., and the acid value ($AV_t$) of the phosphate reaction solution from which phosphorus pentaoxide undissolved in the reaction solution had been removed was measured, and it was confirmed that $AV_t$=192.6 KOH mg/g (theoretical acid value (AV) of the phosphate, 192.7 KOH mg/g; the degree (W) of remaining phosphorus pentaoxide, 0.1 wt %), the reaction solution was heated to 80° C., and an aging reaction was carried as such for 14 hours. The hue of this phosphate was KLETT NO 7, and there was no nasty smell.

The theoretical acid value of the phosphate corresponds to the sum of the theoretical acid values of 85% aqueous phosphoric acid solution and phosphorus pentaoxide added, and can thus be calculated as follows:

Because the theoretical acid value of 85% aqueous phosphoric acid solution=46.6 [g KOH/g] and the theoretical acid value of phosphorus pentaoxide=146.1 [g KOH/g], the theoretical acid value of the phosphate=192.7 [g KOH/g]. The acid value ($AV_t$) of the phosphate reaction solution from which phosphorus pentaoxide undissolved in the reaction solution had been removed was measured by a potentiometric titration method (using 0.5 mol/L aqueous sodium hydroxide solution as a titration solution) with Automatic Potentiometric Titrator AT-510 manufactured by KEM.

Accordingly, the degree (W) of remaining phosphorus pentaoxide undissolved in the reaction solution can be calculated as follows:

$$W=[1-(192.6-46.6)/146.1]\times100=0.1 \text{ [wt \%]}$$

Example 2

The same reaction as in Example 1 was carried out except that after it was confirmed that the acid value ($AV_t$) of the phosphate reaction solution from which phosphorus pentaoxide undissolved in the reaction solution had been removed became 190.7 KOH mg/g (theoretical acid value (AV) of the phosphate, 192.7 KOH mg/g; the degree (w) of remaining undissolved phosphorus pentaoxide, 1.4 wt %), the reaction solution was heated to 80° C. As a result, the hue of this phosphate was KLETT NO 11, and there was no nasty smell.

Example 3

The same reaction as in Example 1 was carried out except that after it was confirmed that the acid value ($AV_t$) of the phosphate reaction solution from which phosphorus pentaoxide undissolved in the reaction solution had been removed became 183.8 KOH mg/g (theoretical acid value (AV) of the phosphate, 192.7 KOH mg/g; the degree (W) of remaining undissolved phosphorus pentaoxide, 6.1 wt %), the reaction solution was heated to 80° C. As a result, the hue of this phosphate was KLETT NO 15, and there was no nasty smell.

Comparative Example 1

The same reaction as in Example 1 was carried out except that after it was confirmed that the acid value ($AV_t$) of the phosphate reaction solution from which phosphorus pentaoxide undissolved in the reaction solution had been removed became 163.4 KOH mg/g (theoretical acid value (AV) of the phosphate, 192.7 KOH mg/g; the degree (W) of remaining undissolved phosphorus pentaoxide, 20.1 wt %), the reaction solution was heated to 80° C. As a result, the hue of this phosphate was as high as KLETT NO 28 to indicate significant coloration, and a nasty smell similar to scorching smell was felt.

Comparative Example 2

In Example 1, 0.22 g phosphorous acid was added as an antioxidant prior to addition of phosphorus pentaoxide. The same reaction as in Example 1 was carried out except that after it was confirmed that the acid value ($AV_t$) of the phosphate reaction solution from which phosphorus pentaoxide undissolved in the reaction solution had been removed became 164.0 KOH mg/g (theoretical acid value (AV) of the phosphate, 192.7 KOH mg/g; the degree (W) of remaining undissolved phosphorus pentaoxide, 20.2 wt %), the reaction solution was heated to 80° C. As a result, the hue of this phosphate was KLETT NO 7, and there was no nasty smell. In analysis by ion chromatography, however, 259 ppm phosphorous acid was detected in the phosphate.

The results in Examples 1 to 3 and Comparative Examples 1 and 2 are collectively shown in Table 1.

TABLE 1

|  |  | Example 1 | Example 2 | Example 3 | Comparative example 1 | Comparative example 2 |
|---|---|---|---|---|---|---|
| Organic hydroxy*[1] | [g] |  |  | 609.9 |  |  |
| 85% Aqueous phosphoric acid solution | [g] |  |  | 81.5 |  |  |
| Phosphorus pentaoxide | [g] |  |  | 158.7 |  |  |
| Antioxidant(phosphorous acid) | [g] | 0 | 0 | 0 | 0 | 0.22 |
| Total amount of the starting materials charged | [g] |  |  | 850.1 |  | 850.3 |
| Reaction temperature before heating | [° C.] |  |  | 65 |  |  |
| Aging reaction temperature after heating | [° C.] |  |  | 80 |  |  |
| AVt when heating was initiated | [KOHmg/g] | 192.6 | 190.7 | 183.8 | 163.4 | 164.0 |
| W when heating was initiated | [wt %] | 0.1 | 1.4 | 6.1 | 20.1 | 20.2 |
| Hue [KLETT NO] |  | 7 | 11 | 15 | 28 | 7 |
| Smell |  | ○ | ○ | ○ | x (scorching smell) | ○ |
| Content of antioxidant | [ppm] | 0 | 0 | 0 | 0 | 259 |

*[1]KALCOL 2470 (manufactured by Kao Corporation), that is, an ethylene oxide (1 mol) adduct.

As is evident from the results shown in Table 1, the phosphate with improvement in hue and suppressed smell can be obtained according to Examples 1 to 3 wherein the reaction solution was heated after the degree (W) of remaining undissolved phosphorus pentaoxide was reduced to 15 wt % or less.

The invention claimed is:

1. A process for producing a phosphate, which comprises the step of reacting a phosphorus pentaoxide-containing phosphorylating agent with an organic hydroxy compound to produce a phosphate, the reaction being carried out at a reaction temperature of 50 to 70° C. until the degree (W) of remaining phosphorus pentaoxide undissolved in a reaction solution, defined by the following equation (1), is reduced to 10 wt % or less:

$$W=[1-(AV_t-AV_p)/AV_0]\times 100 \quad (1)$$

wherein W is the degree [wt %] of remaining phosphorus pentaoxide undissolved in a reaction solution; $AV_t$ is the acid value [mg KOH/g] of the reaction solution excluding undissolved phosphorus pentaoxide in an arbitrary time; $AV_p$ is the theoretical acid value [mg KOH/g] of the phosphorylating agent excluding undissolved phosphorus pentaoxide; and $AV_0$ is the theoretical acid value [mg KOH/g] of phosphorus pentaoxide.

2. The process for producing a phosphate according to claim 1, wherein an aging reaction is further carried out at 75 to 120° C. after the reaction is carried out until the degree (W) of remaining undissolved phosphorus pentaoxide is reduced to 10 wt % or less.

3. The process for producing a phosphate according to claim 1, wherein the organic hydroxy compound comprises an alcohol having a C2 to C4 alkylene oxide added thereto.

4. The process for producing a phosphate according to claim 1, wherein the phosphorylation reaction is carried out in an atmosphere at a low partial pressure of oxygen.

5. A phosphate product having an antioxidant content of 20 ppm or less, produced by the process according to claim 1.

6. The process for producing a phosphate according to claim 2, wherein the organic hydroxy compound comprises an alcohol having a C2 to C4 alkylene oxide added thereto.

7. The process for producing a phosphate according to claim 2, wherein the phosphorylation reaction is carried out in an atmosphere at a low partial pressure of oxygen.

8. A phosphate product having an antioxidant content of 20 ppm or less, produced by the process according to claim 2.

9. The process for producing a phosphate according to claim 1, wherein the reaction is carried out until the degree (W) of remaining phosphorus pentaoxide undissolved in the reaction solution defined by equation (1) is reduced to 5 wt % or less.

* * * * *